United States Patent
Muller et al.

(10) Patent No.: US 11,701,311 B2
(45) Date of Patent: Jul. 18, 2023

(54) DEVICE FOR DISPENSING A HAIR DYEING PRODUCT USING A DYE COMPOSITION AND AN OXIDIZING COMPOSITION COMPRISING A SCLEROGLUCAN GUM

(71) Applicant: L'OREAL, Paris (FR)

(72) Inventors: Sabrina Muller, Saint-Ouen (FR); Delphine Charrier, Saint-Ouen (FR); Aldo Pizzino, Saint-Ouen (FR); Frédéric Simonet, Saint-Ouen (FR); Cindy Yadel, Saint-Ouen (FR); Fanny Cardonnel, Saint-Ouen (FR); Mladen Milic, Saint-Ouen (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/253,019

(22) PCT Filed: Jun. 20, 2019

(86) PCT No.: PCT/EP2019/066361
§ 371 (c)(1),
(2) Date: Dec. 16, 2020

(87) PCT Pub. No.: WO2019/243505
PCT Pub. Date: Dec. 26, 2019

(65) Prior Publication Data
US 2021/0121374 A1    Apr. 29, 2021

(30) Foreign Application Priority Data
Jun. 20, 2018   (FR) ...................... 1855427

(51) Int. Cl.
| A61Q 5/10 | (2006.01) |
| A61K 8/04 | (2006.01) |
| A61K 8/41 | (2006.01) |
| A61K 8/73 | (2006.01) |

(52) U.S. Cl.
CPC ............. *A61K 8/046* (2013.01); *A61K 8/41* (2013.01); *A61K 8/73* (2013.01); *A61Q 5/10* (2013.01)

(58) Field of Classification Search
CPC . A61Q 5/10; A61K 8/22; A61K 8/411; A61K 8/4926; A61K 8/415; A61K 2800/4324; A61K 8/41; A61K 2800/882; A61K 2800/88; A61K 8/347; A61K 8/046; A61K 8/73
USPC ........................................................... 8/405
See application file for complete search history.

(56) References Cited

U.S. PATENT DOCUMENTS

| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,589,978 A | 6/1971 | Kamal et al. |
| 3,632,559 A | 1/1972 | Matter et al. |
| 3,874,870 A | 4/1975 | Green et al. |
| 3,910,862 A | 10/1975 | Barabas et al. |
| 3,912,808 A | 10/1975 | Sokol |
| 3,917,817 A | 11/1975 | Vanlerberghe et al. |
| 3,929,990 A | 12/1975 | Green et al. |
| 3,966,904 A | 6/1976 | Green et al. |
| 4,001,432 A | 1/1977 | Green et al. |
| 4,005,193 A | 1/1977 | Green et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,137,180 A | 1/1979 | Naik et al. |
| 4,157,388 A | 6/1979 | Christiansen |
| 4,165,367 A | 8/1979 | Chakrabarti |

(Continued)

FOREIGN PATENT DOCUMENTS

| CN | 101980750 A | 2/2011 |
| DE | 2359399 A1 | 6/1975 |

(Continued)

OTHER PUBLICATIONS

International Search Report and Written Opinion for counterpart Application No. PCT/EP2019/066365, dated Aug. 13, 2019.
International Search Report and Written Opinion for counterpart Application No. PCT/EP2019/066368, dated Septembers, 2019.
International Search Report and Written Opinion for counterpart Application No. PCT/EP2019/066363, dated Sep. 2, 2019.
International Search Report and Written Opinion for counterpart Application No. PCT/EP2019/066369, dated Aug. 22, 2019.
International Search Report and Written Opinion for counterpart Application No. PCT/EP2019/066364, dated Sep. 11, 2019.

(Continued)

*Primary Examiner* — Eisa B Elhilo
(74) *Attorney, Agent, or Firm* — Marbury Law Group, PLLC.

(57) ABSTRACT

The disclosure relates to a device for dispensing a product for dyeing keratin fibers, comprising a dye composition (A) comprising one or more oxidation dyes and one or more alkaline agents, and an oxidizing composition (B) comprising one or more chemical oxidizing agents, at least one of the compositions (A) and (B) comprising one or more scleroglucan gums in a total weight content greater than or equal to 0.5%, relative to the total weight of the dye composition(s) (A) or the oxidizing composition (B) containing them. Methods for dyeing keratin fibers using the device are also disclosed.

20 Claims, No Drawings

(56) References Cited

U.S. PATENT DOCUMENTS

| | | |
|---|---|---|
| 4,172,887 A | 10/1979 | Vanlerberghe et al. |
| 4,217,914 A | 8/1980 | Jacquet et al. |
| 4,240,450 A | 12/1980 | Grollier et al. |
| 4,349,532 A | 9/1982 | Vanlerberghe et al. |
| 4,381,919 A | 5/1983 | Jacquet et al. |
| 4,591,610 A | 5/1986 | Grollier |
| 4,702,906 A | 10/1987 | Jacquet et al. |
| 4,719,282 A | 1/1988 | Nadolsky et al. |
| 4,761,273 A | 8/1988 | Grollier et al. |
| 4,839,166 A | 6/1989 | Grollier et al. |
| 4,874,554 A | 10/1989 | Lange et al. |
| 4,996,059 A | 2/1991 | Grollier et al. |
| 5,061,289 A | 10/1991 | Clausen et al. |
| 5,089,252 A | 2/1992 | Grollier et al. |
| 5,180,397 A | 1/1993 | Grollier et al. |
| 5,180,399 A | 1/1993 | Grollier et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,766,576 A | 6/1998 | Löwe et al. |
| 6,099,592 A | 8/2000 | Vidal et al. |
| 7,905,926 B2 | 3/2011 | DeGeorge et al. |
| 2004/0034946 A1 | 2/2004 | Legrand et al. |
| 2004/0060125 A1 | 4/2004 | Audouset |
| 2004/0064901 A1 | 4/2004 | Kleen et al. |
| 2004/0133993 A1 | 7/2004 | Cottard et al. |
| 2004/0172771 A1* | 9/2004 | Cottard ............... A61K 8/342 8/405 |
| 2004/0221401 A1 | 11/2004 | Desenne et al. |
| 2005/0039270 A1 | 2/2005 | Legrand et al. |
| 2006/0117493 A1 | 6/2006 | Bureiko et al. |
| 2006/0182697 A1 | 8/2006 | Lalleman et al. |
| 2008/0282481 A1 | 11/2008 | De Boni et al. |
| 2010/0175202 A1 | 7/2010 | Simonet et al. |
| 2010/0192969 A1* | 8/2010 | DeGeorge ............... A61K 8/23 132/208 |
| 2010/0199441 A1 | 8/2010 | Hercouet et al. |
| 2011/0117037 A1 | 5/2011 | Legrand et al. |
| 2011/0150797 A1 | 6/2011 | Legrand et al. |
| 2011/0203605 A1 | 8/2011 | Allard et al. |
| 2011/0203606 A1 | 8/2011 | Recchion et al. |
| 2011/0209720 A1 | 9/2011 | DeGeorge et al. |
| 2012/0076930 A1* | 3/2012 | Miller ............... B05B 7/2472 427/157 |
| 2012/0210523 A1 | 8/2012 | Lalleman et al. |
| 2013/0042883 A1 | 2/2013 | DeGeorge et al. |
| 2013/0167862 A1 | 7/2013 | Lopez et al. |
| 2014/0082855 A1 | 3/2014 | Rapold et al. |
| 2014/0305464 A1 | 10/2014 | DeGeorge et al. |
| 2014/0326270 A1 | 11/2014 | DeGeorge et al. |
| 2015/0143637 A1 | 5/2015 | Rapold et al. |
| 2015/0335545 A1 | 11/2015 | Rapold et al. |
| 2016/0279036 A1* | 9/2016 | Schoepgens ........... A61K 8/361 |
| 2017/0172901 A1 | 6/2017 | Kerl et al. |
| 2017/0354584 A1 | 12/2017 | Lalleman et al. |

FOREIGN PATENT DOCUMENTS

| | | |
|---|---|---|
| DE | 3843892 A1 | 6/1990 |
| DE | 4133957 A1 | 4/1993 |
| DE | 19543988 A1 | 5/1997 |
| EP | 0080976 A1 | 6/1983 |
| EP | 0122324 A1 | 10/1984 |
| EP | 0337354 A1 | 10/1989 |
| EP | 0770375 A1 | 5/1997 |
| FR | 1492597 A | 8/1967 |
| FR | 1583363 A | 10/1969 |
| FR | 2077143 A5 | 10/1971 |
| FR | 2080759 A1 | 11/1971 |
| FR | 2162025 A | 7/1973 |
| FR | 2190406 A2 | 2/1974 |
| FR | 2252840 A1 | 6/1975 |
| FR | 2270846 A1 | 12/1975 |
| FR | 2280361 A2 | 2/1976 |
| FR | 2316271 A1 | 1/1977 |
| FR | 2320330 A1 | 3/1977 |
| FR | 2336434 A1 | 7/1977 |
| FR | 2368508 A2 | 5/1978 |
| FR | 2383660 A1 | 10/1978 |
| FR | 2393573 A1 | 1/1979 |
| FR | 2413907 A1 | 8/1979 |
| FR | 2470596 A1 | 6/1981 |
| FR | 2505348 A1 | 11/1982 |
| FR | 2519863 A1 | 7/1983 |
| FR | 2542997 A1 | 9/1984 |
| FR | 2598611 A1 | 11/1987 |
| FR | 2618070 A1 | 1/1989 |
| FR | 2633940 A1 | 7/1991 |
| FR | 2733749 A1 | 11/1996 |
| FR | 2801308 A1 | 5/2001 |
| FR | 2886136 A1 | 12/2006 |
| FR | 3008615 A1 | 1/2015 |
| GB | 1026978 A | 4/1966 |
| GB | 1153196 A | 5/1969 |
| GB | 1546809 A | 5/1979 |
| GB | 2207443 A | 2/1989 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 96/15765 A1 | 5/1996 |
| WO | 2016/091816 A1 | 6/2016 |
| WO | 2018/056235 A1 | 3/2018 |
| WO | 2019/243505 A1 | 12/2019 |
| WO | 2019/243507 A1 | 12/2019 |
| WO | 2019/243509 A1 | 12/2019 |
| WO | 2019/243511 A1 | 12/2019 |
| WO | 2019/243512 A1 | 12/2019 |
| WO | 2019/243513 A1 | 12/2019 |

OTHER PUBLICATIONS

International Search Report and Written Opinion for counterpart Application No. PCT/EP2019/066361, dated Aug. 22, 2019.
International Search Report and Written Opinion for counterpart Application No. PCT/EP2019/066370, dated Sep. 11, 2019.
Mintel, "Root Vanish," Kazumi, ID 3319563, XP055562798, dated Feb. 27, 2015.
Mintel, "Colourant Cream," LG Household and Health Care, ID 1533817, , XP055547325, dated May 11, 2011.
Mintel, "Hair Colourant," Garnier, ID 644332, XP055547333, dated Jan. 16, 2007.
Final Office Action for copending U.S. Appl. No. 17/252,974, dated Dec. 29, 2021.
Non-Final Office Action for copending U.S. Appl. No. 17/252,856, dated Aug. 16, 2021.
Non-Final Office Action for copending U.S. Appl. No. 17/252,883, dated Aug. 18, 2021.
Non-Final Office Action for copending U.S. Appl. No. 17/253,035, dated Aug. 20, 2021.
Non-Final Office Action for copending U.S. Appl. No. 17/253,007, dated Aug. 25, 2021.
Non-Final Office Action for copending U.S. Appl. No. 17/252,870, dated Sep. 10, 2021.
Non-Final Office Action for copending U.S. Appl. No. 17/252,974, dated Sep. 20, 2021.

* cited by examiner

DEVICE FOR DISPENSING A HAIR DYEING PRODUCT USING A DYE COMPOSITION AND AN OXIDIZING COMPOSITION COMPRISING A SCLEROGLUCAN GUM

CROSS REFERENCE TO RELATED APPLICATION

This is a national stage application of PCT/EP2019/066361, filed internationally on Jun. 20, 2019, which claims priority to French Application No. 1855427, filed on Jun. 20, 2018, both of which are incorporated by reference herein in their entireties.

The present invention relates to a device for dispensing a product for dyeing keratin fibers, comprising a dye composition (A) comprising one or more oxidation dyes, and one or more alkaline agents, and an oxidizing composition (B) comprising one or more chemical oxidizing agents, at least one of the compositions (A) and/or (B) comprising one or more scleroglucan gums preferably in a total weight content of greater than or equal to 0.5% relative to the total weight of composition(s) (A) and/or (B) containing same, and also to a process for dyeing keratin fibers using said device.

The present invention relates to the field of dyeing keratin fibers and more particularly to the field of hair dyeing, in particular oxidation dyeing.

Among the methods for dyeing human keratin fibers, such as the hair, mention may be made of oxidation dyeing or permanent dyeing. More particularly, this form of dyeing uses one or more oxidation dyes, usually one or more oxidation bases optionally combined with one or more couplers.

The variety of molecules used as oxidation bases and couplers allows a wide range of colors to be obtained.

Oxidation dyeing processes thus consist in using with these dye compositions a composition comprising at least one oxidizing agent, generally hydrogen peroxide, under alkaline pH conditions in the vast majority of cases. The role of this oxidizing agent is to reveal the coloring, via an oxidative condensation reaction between the oxidation dyes.

These compositions, in particular compositions comprising oxidation dyes, are obviously oxidation-sensitive and consequently contain reducing agents or antioxidants. This protective action against oxidation is also reinforced by means of the inert atmosphere that is occasionally used during the packaging of these compositions.

The difficulty encountered with compositions of this type results, precisely, from their oxidation-sensitivity. Specifically, during their use, they are placed in contact with atmospheric oxygen and this then requires them to be used rapidly. If this does not happen, the compositions become unusable after storage and are lost.

In the field of hair dyeing, alkaline compositions, in particular dye compositions, and oxidizing compositions exist which are packaged separately in the same pressurized container and which make it possible to prevent the composition from coming into contact with air during their use. These compositions may be in mousse or cream form.

However, the coloring power and the coverage of the hair, in particular of gray hair, still remain to be improved, as do the rheological properties of the product(s) obtained from the pressurized container, notably as regards the ease of mixing of the alkaline and oxidizing compositions, the homogeneity of the mixture and the quality of application to the keratin fibers (in particular as regards the wetting nature, the adhesion to the roots and the ease of extension of the mixture along the locks of hair).

There is a constant need to develop devices for dispensing dye compositions while at the same time conserving the usual values.

Oxidation dyeing must moreover satisfy a certain number of requirements. Thus, it must be free of toxicological drawbacks, it must enable shades to be obtained in the desired intensity and it must show a good wear property in the face of external attacking factors such as light, bad weather, washing, permanent waving, perspiration and rubbing.

The dyeing process must also make it possible to cover gray hair and, finally, must be as unselective as possible, i.e. it must produce the smallest possible color differences along the same keratin fiber, which generally includes areas that are differently sensitized (i.e. damaged) from its end to its root, so as to obtain the most uniform possible coloring of the keratin fibers. Dye compositions must also give good cosmetic properties to keratin fibers, in particular care, softness and/or hold, and must have good working qualities, in particular they must be easy to apply, while at the same time achieving visible (i.e. notably intense, chromatic), uniform and fast coloring results.

The compositions used in a dyeing process must also have good mixing and application properties on keratin fibers, and notably good rheological properties so as not to run down onto the face, onto the scalp or beyond the areas that it is proposed to dye, when they are applied; this notably allows uniform application from the roots to the ends.

In particular, it is sought to obtain dye compositions or oxidizing compositions that are stable over time for several weeks. For the purposes of the present invention, the term "stable" in particular means that physical properties such as the appearance, the pH and/or the viscosity vary little or not at all over time, and in particular that the viscosity of the composition does not change or changes little during storage and/or that the composition does not undergo phase separation during storage.

Specifically, it is desirable for the dye compositions or oxidizing compositions to be stable over time, in particular stable after 1 month at 45° C., or even after 2 months at 45° C.

It is also sought to obtain dye compositions that are stable over a wide pH range and in particular with respect to extreme pH values, for example to alkaline pH values ranging from 9 to 12. Finally, the dye compositions may occasionally be destabilized (undergo phase separation) by high contents of certain compounds, for instance oxidation dyes and/or cationic compounds such as cationic polymers, and it is thus desirable for these compositions to be stable under these conditions, in particular for them not to undergo phase separation.

Thus, one of the objects of the present invention is to propose a process for dyeing keratin fibers, preferably human keratin fibers such as the hair, which do not have the drawbacks mentioned above.

These aims and others are achieved by the present invention, one subject of which is thus a device for dispensing a product for dyeing keratin fibers, consisting of a container, preferably in aerosol form, comprising:

i) at least two compartments (a) and (b) which are separate from each other, compartment (a) comprising a composition (A) comprising:
one or more oxidation dyes;
one or more alkaline agents; and compartment (b) comprising an oxidizing composition B comprising:
one or more chemical oxidizing agents, preferably chosen from hydrogen peroxide and/or one or more systems for generating hydrogen peroxide, preferably hydrogen peroxide; and
one and/or the other of compositions (A) and/or (B) comprising one or more scleroglucan gums, preferably in a total weight content of greater than or equal to 0.5% relative to the total weight of composition(s) (A) and/or (B) containing same;

ii) a dispensing means equipped with at least one dispensing orifice, in communication with compartments (a) and (b), for simultaneously dispensing compositions (A) and (B), in mixed or separate form.

Preferably, compositions (A) and (B) comprise one or more scleroglucan gums, preferably in a total weight content of greater than or equal to 0.5% relative to the total weight of composition(s) (A) and (B) containing same.

A subject of the invention is also a process for dyeing keratin fibers, preferably human keratin fibers, using this device.

More precisely, a subject of the invention is a process for dyeing keratin fibers, preferably human keratin fibers such as the hair, involving the application to the fibers:

a) of a dye composition (A) comprising:
one or more oxidation dyes;
one or more alkaline agents; and b) of an oxidizing composition (B) comprising:
one or more chemical oxidizing agents, preferably chosen from hydrogen peroxide and/or one or more systems for generating hydrogen peroxide, preferably from hydrogen peroxide; and
one and/or the other of compositions (A) and/or (B) comprising one or more scleroglucan gums, preferably in a total weight content of greater than or equal to 0.5% relative to the total weight of composition(s) (A) and/or (B) containing same;
compositions (A) and (B) being packaged in a device consisting of a container, preferably a pressurized container, comprising at least two compartments (a) and (b) which are separated from each other, compartment (a) comprising composition (A) and compartment (b) comprising composition (B), the device comprising a dispensing means equipped with at least one dispensing orifice, in communication with compartments (a) and (b), for dispensing compositions (A) and (B) simultaneously.

For the purposes of the present invention, the term "composition for dyeing" or "dye composition" means a composition intended to be applied to keratin fibers, preferably human keratin fibers and in particular the hair, in particular after mixing with an oxidizing composition (B) as defined previously.

For the purposes of the present invention, the term "ready-to-use dye composition" or "ready-to-use composition" means a composition resulting from mixing a dye composition and an oxidizing composition, intended to be applied immediately to the keratin fibers. The ready-to-use dye composition is advantageously prepared just before application to said keratin fibers.

The device and the process of the invention afford good dyeing properties on keratin fibers, notably in terms of build-up, intensity, chromaticity and/or selectivity. They also afford compositions which have good rheological properties so as not to run down onto the face, the scalp or beyond the areas that it is proposed to dye, when they are applied.

The compositions used in the process according to the invention are stable. For the purposes of the present invention, the term "stable" in particular means that physical properties such as the appearance, the pH and/or the viscosity vary little or not at all over time, and in particular that the viscosity of the composition does not change or changes little during storage and/or that the composition does not undergo phase separation during storage. In particular, it is desirable for the dye compositions to be stable over time, in particular stable after 1 month at 45° C., or even after 2 months at 45° C.

Furthermore, the compositions used according to the invention have the advantage of being stable (of not undergoing phase separation) independently of the pH and in particular with respect to extreme pH values (for example alkaline pH values ranging from 9 to 12). Finally, the compositions are preferably stable (do not undergo phase separation) even in the presence of a high content of certain compounds, for instance oxidation dyes and/or cationic compounds, such as cationic polymers.

Moreover, the compositions used in the device and the process according to the invention are advantageously translucent, which gives them a visual appearance that is esthetic and appealing to the consumer, as is the ready-to-use composition resulting from the mixing of the dye composition (A) and the oxidizing composition (B), during the implementation of the process according to the invention.

This translucent ready-to-use dye composition offers the possibility of visualizing the change in the color result during the time that the product is left on, affording the choice of stopping at the moment that the result is suitable.

The device comprising the compositions also leads to good working qualities; in particular, compositions (A) and (B) are easy to apply and are uniformly distributed along the keratin fibers.

The device and the process of the invention also lead to good cosmetic properties, notably in terms of disentangling, suppleness and softness of the hair.

In addition, compositions (A) and (B) used according to the invention mix together easily, prior to application to the keratin fibers or directly on the keratin fibers during simultaneous application of compositions (A) and (B) to the hair.

Furthermore, by virtue of their very stable and similar rheological properties, the dye compositions and oxidizing compositions used allow the use of packaging in the device according to the invention for the implementation of the process according to the invention.

Specifically, in the context of the use of a dispensing device according to the invention, it is necessary for the viscosities of compositions (A) and (B) to be stable, and preferably similar, so that the amount of composition (A) and (B) simultaneously dispensed remains stable over time, which might not be the case if the viscosity of one of the compositions proved not to be stable. Furthermore, since the mixing takes place during the dispensing or directly on the keratin fibers during application, it is necessary for the compositions to mix together readily.

Other features and advantages of the invention will emerge more clearly on reading the description and the examples that follow.

In the text hereinbelow, unless otherwise indicated, the limits of a range of values are included in that range, notably in the expressions "between" and "ranging from . . . to . . . ".

The keratin fibers are preferably human keratin fibers, preferably the hair.

The expression "at least one" is equivalent to the expression "one or more".

Advantageously, the dye composition and the oxidizing composition used in the process according to the invention have a thickened texture, in cream or gel form, and are preferably translucent.

Compositions (A) and (B) used in the process and the device according to the invention generally have at room temperature a viscosity of greater than 50 cps, preferably between 200 and 100 000 cps, more preferentially between 400 and 50 000 cps and even more preferentially between 500 and 10 000 cps, better still from 600 to 8000 cps. This viscosity is measured at 25° C. at a spin speed of 200 rpm using a rheometer such as a Rheomat RM 180 equipped with a No. 3 or 4 spindle, the measurement being performed after 60 seconds of rotation of the spindle (after which time stabilization of the viscosity and of the spin speed of the spindle are observed).

According to a particular embodiment, the viscosity of each of the two compositions is between 500 to 10 000 cps, better still from 600 to 8000 cps.

Dye Composition (A)

Oxidation Dyes

The dye composition (A) according to the invention comprises one or more oxidation dyes.

The oxidation dye precursors that may be used in the present invention are generally chosen from oxidation bases, optionally combined with one or more couplers.

The oxidation bases may preferably be chosen from para-phenylenediamines, bis(phenyl)alkylenediamines, para-aminophenols, ortho-aminophenols and heterocyclic bases, and the addition salts thereof.

Preferentially, the oxidation base(s) of the invention are chosen from para-phenylenediamines and heterocyclic bases. Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, 2-methoxymethyl-para-phenylenediamine, N,N-dimethyl-3-methyl-para-phenylenediamine, N-ethyl-N-(β-hydroxyethyl)-para-phenylenedi amine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenedi amine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine and 2-methoxymethyl-para-phenylenediamine, and the addition salts thereof with an acid, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols, examples that may be mentioned include 2-aminophenol, 2-amino-5-methylphenol, 2-amino-6-methylphenol, 5-acetamido-2-aminophenol and the addition salts thereof.

Among the heterocyclic bases, mention may be made in particular of pyridine derivatives, pyrimidine derivatives and pyrazole derivatives.

Among the pyridine derivatives, mention may be made of the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxy ethyl)amino]ethanol, 2-[(3-aminopyrazolo pyrid-7-yl)(2-hydroxy ethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-β-hydroxy ethoxy-3-aminopyrazolo[1,5-a]pyridine and 2-(4-dimethylpiperazinium-1-yl)-3-aminopyrazolo[1,5-a] pyridine, and also the addition salts thereof.

More particularly, the oxidation bases according to the invention are chosen from 3-aminopyrazolo[1,5-a]pyridines preferably substituted in position 2 with:

a) a (di)($C_1$-$C_6$)(alkyl)amino group, the alkyl groups possibly being substituted with one or more hydroxyl, amino or imidazolium groups;

b) a cationic or non-cationic 5- to 7-membered heterocycloalkyl group comprising from 1 to 3 heteroatoms, optionally substituted with one or more ($C_1$-$C_6$)alkyl groups such as di($C_1$-$C_4$)alkylpiperazinium;

c) a ($C_1$-$C_6$)alkoxy group optionally substituted with one or more hydroxyl groups, such as β-hydroxyalkoxy, and also the addition salts thereof.

Among the pyrimidine derivatives, mention may be made of the compounds described, for example, in patents DE 2359399, JP 88169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof, and the tautomeric forms thereof, when a tautomeric equilibrium exists.

Among the pyrazole derivatives mention may be made of the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof. Preferably, the heterocyclic oxidation bases of the invention are chosen from 4,5-diaminopyrazoles such as 4,5-diamino-1-(β-hydroxyethyl)pyrazole. Use may also be made of 4,5-diamino-1-(β-methoxyethyl)pyrazole.

Use will preferably be made of a 4,5-diaminopyrazole and even more preferentially of 4,5-diamino-1-(β-hydroxyethyl)pyrazole and/or a salt thereof.

Pyrazole derivatives that may also be mentioned include diamino-N,N-dihydropyrazolopyrazolones and notably those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-bis(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a salt thereof.

As heterocyclic bases, use will preferentially be made of 4,5-diamino-1-(β-hydroxyethyl)pyrazole and/or 2,3-diamino-6,7-dihydro-1H,5H-pyrazolo[1,2-a]pyrazol-1-one and/or a salt thereof.

The oxidation base(s) used in the context of the invention are generally present in an amount ranging from 0.001% to 10% by weight approximately, preferably ranging from 0.005% to 5%, relative to the total weight of the dye composition.

The additional couplers that are conventionally used for the dyeing of keratin fibers are preferably chosen from meta-phenylenediamines, meta-aminophenols, meta-diphenols, naphthalene-based couplers and heterocyclic couplers, and also the addition salts thereof.

Examples that may be mentioned include 1,3-dihydroxybenzene, 1,3-dihydroxy-2-methylbenzene, 4-chloro-1,3-dihydroxybenzene, 1-hydroxy-3-aminobenzene, 2-methyl-5-aminophenol, 3-amino-2-chloro-6-methylphenol, 2-methyl-5-hydroxyethylaminophenol, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, thymol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the invention are notably chosen from the addition salts with an acid, such as hydrochlorides, hydrobromides, sulfates, citrates, succinates, tartrates, lactates, tosylates, benzenesulfonates, phosphates and acetates.

In the context of the present invention, when they are present, the coupler(s) are generally present in a total amount ranging from 0.001% to 10% by weight approximately of the total weight of the dye composition, and preferably ranging from 0.005% to 5% by weight relative to the total weight of the dye composition (A).

Preferably, the total content of oxidation dyes in the composition according to the invention is between 0.001% and 20% by weight, preferably between 0.001% and 10% by weight, preferably between 0.01% and 5% by weight, relative to the weight of the dye composition (A).

Scleroglucan Gums

According to the invention, composition (A) preferably comprises one or more scleroglucan gums preferably in a total content of greater than or equal to 0.5% by weight relative to the weight of composition (A).

Scleroglucan gums are polysaccharides of microbial origin produced by a fungus of *Sclerotium* type, in particular *Sclerotium rolfsii*. They are polysaccharides constituted solely of glucose units.

Scleroglucan gums may or may not be modified. Preferably, the scleroglucan gums used in the present invention are unmodified.

Examples of scleroglucan gums that may be used in the present invention are, in a nonlimiting manner, the products sold under the name Actigum CS, in particular Actigum CS 11 by the company Sanofi Bio Industries, and under the name Amigum or Amigel by the company Alban Müller International.

Other scleroglucan gums, such as the gum treated with glyoxal described in French patent application No. 2 633 940, may also be used.

When composition (A) comprises one or more scleroglucan gums, their total content preferably represents from 0.5% to 10% by weight, more preferentially from 0.5% to 5% by weight, even more preferentially from 0.5% to 3% by weight, better still from 0.5% to 2% by weight and even more preferentially from 0.7% to 1.5% by weight, relative to the total weight of composition (A).

In a preferred embodiment of the invention, composition (A) comprises one or more scleroglucan gums, preferably in a total content of greater than or equal to 0.5% by weight relative to the weight of composition (A).

More preferentially, composition (A) comprises one or more scleroglucan gums in a total content of greater than or equal to 0.5%, preferably from 0.5% to 10% by weight, more preferentially from 0.5% to 5% by weight, even more preferentially from 0.5% to 3% by weight, better still from 0.5% to 2% by weight and even more preferentially from 0.7% to 1.5% by weight, relative to the total weight of composition (A).

Alkaline Agents

Composition (A) used in the process according to the invention comprises one or more alkaline agents. The alkaline agent(s) (also known as basifying agents) may be mineral, organic and/or hybrid, in particular mineral and/or organic.

According to a first advantageous embodiment of the invention, the alkaline agent(s) are chosen from mineral alkaline agent(s), preferably chosen from aqueous ammonia, also known as ammonium hydroxide (or ammonia precursors such as ammonium salts, for example ammonium halides and in particular ammonium chloride), alkali metal or alkaline-earth metal silicates, phosphates, carbonates or bicarbonates, such as alkali metal or alkaline-earth metal metasilicates, sodium or potassium carbonate or bicarbonate, sodium or potassium hydroxide, or mixtures thereof.

Preferably according to this embodiment, the alkaline agents are chosen from aqueous ammonia (or ammonia precursors such as ammonium salts, for example ammonium halides and in particular ammonium chloride) and/or alkali metal or alkaline-earth metal metasilicates.

According to a second advantageous embodiment of the invention, the alkaline agent(s) are chosen from organic alkaline agent(s), preferably chosen from organic amines with a $pK_b$ at 25° C. of less than 12, preferably of less than 10 and even more advantageously of less than 6. It should be noted that it is the $pK_b$ corresponding to the function which has the highest basicity. In addition, the organic amines do not comprise any alkyl or alkenyl fatty chains comprising more than ten carbon atoms.

According to a preferred embodiment, the organic alkaline agent(s) are chosen from alkanolamines and/or amino acids.

According to a first preferred embodiment, the alkaline agent(s) are chosen from alkanolamines.

The term "alkanolamine" means an organic amine comprising a primary, secondary or tertiary amine function, and one or more linear or branched $C_1$ to $C_8$ alkyl groups bearing one or more hydroxyl radicals.

Organic amines chosen from alkanolamines such as monoalkanolamines, dialkanolamines or trialkanolamines comprising one to three identical or different $C_1$ to $C_4$ hydroxyalkyl radicals are in particular suitable for performing the invention.

The compounds of this type are preferably chosen from monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane, and mixtures thereof, preferably monoethanolamine (MEA).

According to a second preferred embodiment, the alkaline agent(s) are chosen from amino acids.

More particularly, the amino acids that may be used are of natural or synthetic origin, in their L, D or racemic form, and include at least one acid function chosen more particularly from carboxylic acid, sulfonic acid, phosphonic acid and phosphoric acid functions. The amino acids may be in neutral or ionic form.

As amino acids that may be used in the composition according to the present invention, mention may notably be made of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are chosen from basic amino acids, notably comprising an additional amine function optionally included in a ring or in a ureido function.

Such basic amino acids are preferably chosen from histidine, lysine, arginine, ornithine and citrulline.

According to a particularly preferred embodiment of the invention, composition (A) comprises:
one or more mineral alkaline agents, preferably chosen from aqueous ammonia and/or alkali metal or alkaline-earth metal metasilicates, preferably aqueous ammonia; and
one or more organic alkaline agents, preferably chosen from alkanolamines and/or amino acids, preferably from alkanolamines, preferably monoethanolamine.

Composition (A) according to the invention preferably comprises one or more mineral alkaline agents and one or more alkaline agents chosen from alkanolamine(s).

When composition (A) comprises aqueous ammonia (ammonium hydroxide), its content preferably ranges from 0.1% to 10% by weight, more preferentially from 0.5% to 8% by weight and better still from 1% to 6% by weight, relative to the total weight of composition (A).

When composition (A) comprises one or more alkanolamines, their content preferably ranges from 0.5% to 10% by weight, more preferentially from 1% to 9% by weight and better still from 2% to 8% by weight relative to the total weight of composition (A).

Preferably, the dye composition (A) according to the invention comprises a total content of alkaline agents ranging from 1% to 20% by weight, more preferentially from 3% to 18% by weight and better still from 5% to 16% by weight relative to the total weight of composition (A).

Associative Polymers

The dye composition (A) according to the invention may also comprise one or more associative polymers. The associative polymers according to the invention are polymers comprising at least one $C_8$-$C_{30}$ fatty chain and of which the molecules are capable, in the formulation medium, of associating with each other or with molecules of other compounds.

Preferably, the fatty chain includes from 10 to 30 carbon atoms.

A particular case of associative polymers is amphiphilic polymers, i.e. polymers including one or more hydrophilic parts which make them water-soluble and one or more hydrophobic zones (comprising at least one fatty chain) via which the polymers interact and assemble with each other or with other molecules.

The associative polymers that may be used in the composition according to the invention may be chosen from nonionic, anionic, cationic and amphoteric associative polymers, and mixtures thereof.

Particularly preferably, the associative polymer(s) are nonionic, and preferably chosen from celluloses modified with groups including at least one fatty chain. Preferably, the nonionic associative polymer(s) are chosen from hydroxyethylcelluloses modified with groups including at least one fatty chain, such as alkyl, arylalkyl or alkylaryl groups, or mixtures thereof, and in which the alkyl groups are preferably $C_8$-$C_{22}$, and hydroxyethylcelluloses modified with polyalkylene glycol alkyl phenyl ether groups, and mixtures thereof, preferably cetylhydroxyethylcellulose.

Cationic Polymers

According to an advantageous embodiment of the invention, composition (A) comprises one or more cationic polymers, other than the cationic fixing polymers mentioned previously, and other than the cationic associative polymers mentioned previously.

As cationic polymers that may be used in the compositions according to the invention, mention may be made in particular of:
(1) cyclopolymers of alkyldiallylamine or of dialkyldiallylammonium, such as the homopolymers or copolymers including, as main constituent of the chain, units corresponding to formula (I) or (II):

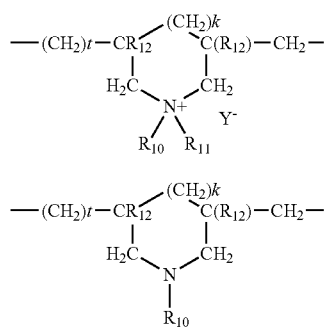

in which
k and t are equal to 0 or 1, the sum k+t being equal to 1;
R12 denotes a hydrogen atom or a methyl radical;
R10 and R11, independently of each other, denote a C1-C6 alkyl group, a C1-C5 hydroxyalkyl group, a C1-C4 amidoalkyl group; or alternatively R10 and R11 may denote, together with the nitrogen atom to which they are attached, a heterocyclic group such as piperidyl or morpholinyl; R10 and R11, independently of each other, preferably denote a C1-C4 alkyl group;

$Y^-$ is an anion such as bromide, chloride, acetate, borate, citrate, tartrate, bisulfate, bisulfite, sulfate or phosphate. Mention may be made more particularly of the dimethyldiallylammonium salt (for example chloride) homopolymer, for example sold under the name Merquat 100 by the company Nalco. Preferably, the polymers of family (1) are chosen from dialkyldiallylammonium homopolymers.

(2) quaternary diammonium polymers comprising repeating units of formula:

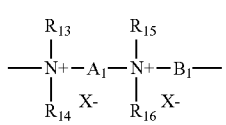

in which:
R13, R14, R15 and R16, which may be identical or different, represent aliphatic, alicyclic or arylaliphatic radicals comprising from 1 to 20 carbon atoms or C1-C12 hydroxyalkyl aliphatic radicals, or else R13, R14, R15 and R16, together or separately, form, with the nitrogen atoms to which they are attached, heterocycles optionally comprising a second non-nitrogen heteroatom;

or else R13, R14, R15 and R16 represent a linear or branched C1-C6 alkyl radical substituted with a nitrile, ester, acyl, amide or —CO—O—R17-D or —CO—NH—R17-D group, where R17 is an alkylene and D is a quaternary ammonium group;

A1 and B1 represent linear or branched, saturated or unsaturated, divalent polymethylene groups comprising from 2 to 20 carbon atoms, which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from a mineral or organic acid;
it being understood that A1, R13 and R15 can form, with the two nitrogen atoms to which they are attached, a piperazine ring;
in addition, if A1 denotes a linear or branched, saturated or unsaturated alkylene or hydroxyalkylene radical, B1 may also denote a group (CH2)n-CO-D-OC—(CH2)p- with n and p, which may be identical or different, being integers ranging from 2 to 20, and D denoting:

a) a glycol residue of formula —O—Z—O—, in which Z denotes a linear or branched hydrocarbon-based radical or a group corresponding to one of the following formulae: —(CH2CH2O)x-CH2CH2- and —[CH2CH(CH3)O]y-CH2CH(CH3)-, in which x and y denote an integer from 1 to 4, representing a defined and unique degree of polymerization or any number from 1 to 4 representing an average degree of polymerization;

b) a bis-secondary diamine residue, such as a piperazine derivative;

c) a bis-primary diamine residue of formula —NH—Y—NH—, in which Y denotes a linear or branched hydrocarbon-based radical, or else the divalent radical —CH2-CH2-S—S—CH2-CH2-;

d) a ureylene group of formula —NH—CO—NH—.

Preferably, X⁻ is an anion, such as chloride or bromide.

These polymers have a number-average molar mass (Mn) generally of between 1000 and 100 000.

Mention may be made more particularly of cationic polymers that are constituted of repeating units corresponding to the formula:

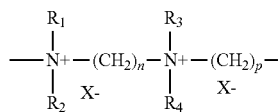

in which R1, R2, R3 and R4, which may be identical or different, denote an alkyl or hydroxyalkyl radical containing from 1 to 4 carbon atoms, n and p are integers ranging from 2 to 20, and X− is an anion derived from a mineral or organic acid. A particularly preferred compound of formula (IV) is the one for which R1, R2, R3 and R4 represent a methyl radical, n=3, p=6 and X=Cl, known as Hexadimethrine chloride according to the INCI (CTFA) nomenclature.

Preferably, the cationic polymer(s) are chosen from dialkyldiallylammonium homopolymers, in particular homopolymers of dimethyldiallylammonium salts, polymers constituted of repeating units corresponding to formula (IV) above, in particular poly(dimethyliminio)-1,3-propanediyl (dimethyliminio)-1,6-hexanediyl dichloride, the INCI name of which is hexadimethrine chloride, and mixtures thereof.

When they are present, the total content of cationic polymers (other than the associative polymers and the fixing polymers) in composition (A) may range from 0.01% to 10% by weight relative to the weight of the composition, preferably from 0.1% to 7% relative to the weight of the composition, even more advantageously from 0.5% to 5% by weight and better still from 0.5% to 3% by weight relative to the weight of composition (A).

Surfactants

Preferably, composition (A) comprises one or more surfactants, which may be chosen from anionic surfactants, amphoteric or zwitterionic surfactants, nonionic surfactants and cationic surfactants, and mixtures thereof, preferably from nonionic surfactants, cationic surfactants, and mixtures thereof.

The nonionic surfactants that may be used according to the invention may be chosen from:
alcohols, α-diols and ($C_1$-$C_{20}$)alkylphenols, these compounds being polyethoxylated and/or polypropoxylated and/or polyglycerolated, the number of ethylene oxide and/or propylene oxide groups possibly ranging from 1 to 100, and the number of glycerol groups possibly ranging from 2 to 30; or else these compounds comprising at least one fatty chain including from 8 to 40 carbon atoms and notably from 16 to 30 carbon atoms; in particular, oxyethylenated alcohols comprising at least one saturated or unsaturated, linear or branched $C_8$ to $C_{40}$ alkyl chain, comprising from 1 to 100 mol of ethylene oxide, preferably from 2 to 50 and more particularly from 2 to 40 mol of ethylene oxide and including one or two fatty chains;
condensates of ethylene oxide and propylene oxide with fatty alcohols;
polyethoxylated fatty amides preferably containing from 2 to 30 ethylene oxide units, polyglycerolated fatty amides including on average from 1 to 5 and in particular from 1.5 to 4 glycerol groups;
ethoxylated fatty acid esters of sorbitan, preferably containing from 2 to 40 ethylene oxide units;
fatty acid esters of sucrose;
polyoxyalkylenated, preferably polyoxyethylenated, fatty acid esters containing from 2 to 150 mol of ethylene oxide, including oxyethylenated plant oils;
N—($C_6$-$C_{24}$ alkyl)glucamine derivatives;
amine oxides such as ($C_{10}$-$C_{14}$ alkyl)amine oxides or N—($C_{10}$-$C_{14}$ acyl)aminopropylmorpholine oxides;
and mixtures thereof.

Mention may also be made of nonionic surfactants of alkyl(poly)glycoside type.

Among the commercial products, mention may be made of the products sold by the company Cognis under the names Plantaren® (600 CS/U, 1200 and 2000) or Plantacare® (818, 1200 and 2000); the products sold by the company SEPPIC under the names Oramix CG 110 and Oramix® NS 10; the products sold by the company BASF under the name Lutensol GD 70, or the products sold by the company Chem Y under the name AG10 LK.

Preferably, use is made of $C_8$/$C_{16}$-alkyl (poly)glycosides 1,4, notably as an aqueous 53% solution, such as those sold by Cognis under the reference Plantacare® 818 UP.

Preferentially, the nonionic surfactants are chosen from:
saturated or unsaturated, linear or branched, oxyethylenated fatty alcohols including at least one $C_8$ to $C_{40}$, notably $C_8$-$C_{20}$ and better still $C_{10}$-$C_{18}$ alkyl chain, and comprising from 1 to 100 mol of ethylene oxide, preferably from 2 to 50, more particularly from 2 to 40 mol, or even from 3 to 20 mol of ethylene oxide; and
($C_6$-$C_{24}$ alkyl)(poly)glycosides, and more particularly ($C_8$-$C_{18}$ alkyl)(poly)glycosides;
and mixtures thereof;
and even more preferentially from ($C_6$-$C_{24}$ alkyl)(poly)glycosides, preferentially ($C_8$-$C_{18}$ alkyl)(poly)glycosides.

According to a first embodiment, the surfactant(s) are nonionic, preferably chosen from ($C_6$-$C_{24}$ alkyl)polyglycosides.

According to a preferred embodiment, composition (A) comprises at least one or more cationic surfactants. Preferably, the cationic surfactant(s) are chosen from optionally polyoxyalkylenated primary, secondary or tertiary fatty amine salts, quaternary ammonium salts, and mixtures thereof.

Use may also be made of the behenoylhydroxypropyltrimethylammonium chloride sold, for example, by the company Kao under the name Quartamin BTC 131.

Preferably, the ammonium salts containing at least one ester function contain two ester functions.

Preferably, the cationic surfactant(s) are chosen from cetyltrimethylammonium, behenyltrimethylammonium and dipalmitoyl-ethylhydroxyethylmethylammonium salts, and mixtures thereof, and more particularly behenyltrimethylammonium chloride, cetyltrimethylammonium chloride, and dipalmitoylethylhydroxyethylammonium methosulfate, and mixtures thereof.

Composition (A) preferably comprises one or more surfactants in a total content ranging from 0.01% to 20% by weight, more preferentially from 0.05% to 10% by weight and better still from 0.1% to 5% by weight, relative to the total weight of composition (A).

Composition (A) preferably comprises one or more nonionic surfactants in a total content ranging from 0.01% to 10% by weight, more preferentially from 0.05% to 5% by weight and better still from 0.1% to 3% by weight, relative to the total weight of composition (A).

Composition (A) preferably comprises one or more cationic surfactants in a total content ranging from 0.01% to 10% by weight, more preferentially from 0.05% to 5% by weight and better still from 0.1% to 3% by weight, relative to the total weight of composition (A).

Preferably, the surfactant(s) are chosen from cationic or nonionic surfactants, and mixtures thereof, preferentially cationic surfactants. Preferably, composition (A) comprises at least one or more cationic surfactants and one or more nonionic surfactants.

Oxidizing Composition (B)

Oxidizing Agents:

The oxidizing composition (B) used according to the invention contains one or more chemical oxidizing agents, preferably chosen from hydrogen peroxide and/or one or more systems for generating hydrogen peroxide.

The term "chemical oxidizing agent" means an oxidizing agent other than atmospheric oxygen.

Preferably, the chemical oxidizing agent(s) are chosen from hydrogen peroxide, peroxygenated salts, for instance persulfates, perborates, peracids and precursors thereof, percarbonates of alkali metals or alkaline-earth metals, such as sodium carbonate peroxide, also known as sodium percarbonate and peracids and precursors thereof; alkali metal bromates or ferricyanides, solid hydrogen peroxide-generating chemical oxidizing agents such as urea peroxide and polymer complexes that can release hydrogen peroxide, notably those comprising a heterocyclic vinyl monomer such as polyvinylpyrrolidone/$H_2O_2$ complexes, in particular in powder form; oxidases that produce hydrogen peroxide in the presence of a suitable substrate (for example glucose in the case of glucose oxidase or uric acid with uricase).

Preferably, the chemical oxidizing agent(s) are chosen from hydrogen peroxide, urea peroxide, alkali metal bromates or ferricyanides, peroxygenated salts, and mixtures of these compounds.

Particularly preferably, the chemical oxidizing agent is hydrogen peroxide.

Preferably, the chemical oxidizing agent(s) represent from 0.05% to 40% by weight, preferably from 0.5% to 30% by weight, more preferentially from 1% to 20% by weight and better still from 1.5% to 15% by weight relative to the total weight of the oxidizing composition (B).

Preferably, the oxidizing composition (B) according to the invention does not contain any peroxygenated salts.

As indicated previously, the oxidizing composition (B) may comprise one or more scleroglucan gums, preferably in a total content of greater than or equal to 0.5% by weight relative to the weight of the composition.

Preferably, when composition (B) comprises one or more scleroglucan gums, their total content preferably represents from 0.5% to 10% by weight, more preferentially from 0.5% to 5% by weight, and even more preferentially from 0.5% to 3% by weight or even from 0.7% to 2% by weight, relative to the total weight of the oxidizing composition (B).

According to a preferred embodiment of the invention, the oxidizing composition (B) comprises one or more scleroglucan gums, preferably in a total content of greater than or equal to 0.5% by weight.

More preferentially, the oxidizing composition (B) comprises one or more scleroglucan gums in a total content of greater than or equal to 0.5% by weight, preferably from 0.5% to 10% by weight, more preferentially from 0.5% to 5% by weight, and even more preferentially from 0.5% to 3% by weight or even from 0.7% to 2% by weight, relative to the total weight of the oxidizing composition (B).

The oxidizing composition (B) may also contain various additional compounds or various adjuvants conventionally used in hair dye compositions, notably as defined previously, in particular such as one or more surfactants as described previously.

This oxidizing composition (B) may also comprise one or more water-soluble organic solvents as described below.

Finally, the oxidizing composition (B) is in various forms, for instance a solution, an emulsion or a gel.

Medium

The compositions used according to the invention are cosmetically acceptable and consequently comprise a cosmetically acceptable medium.

The term "cosmetically acceptable medium" means a medium that is compatible with keratin fibers.

The cosmetically acceptable medium that is suitable for dyeing keratin fibers, also known as a dye support, generally comprises water or a mixture of water and of at least one organic solvent to dissolve the compounds that are not sufficiently water-soluble.

More particularly, the organic solvents are chosen from linear or branched and preferably saturated monoalcohols or diols, comprising from 2 to 10 carbon atoms, such as ethyl alcohol, isopropyl alcohol, hexylene glycol (2-methyl-2,4-pentanediol), neopentyl glycol and 3-methyl-1,5-pentanediol; glycerol; aromatic alcohols such as benzyl alcohol and phenylethyl alcohol; glycols or glycol ethers, for instance ethylene glycol monomethyl, monoethyl and monobutyl ethers, propylene glycol or ethers thereof, for instance propylene glycol monomethyl ether, butylene glycol or dipropylene glycol; and also diethylene glycol alkyl ethers, notably of $C_1$-$C_4$, for instance diethylene glycol monoethyl ether or monobutyl ether, alone or as a mixture.

The common solvents described above, if they are present, usually represent from 1% to 40% by weight and more preferentially from 5% to 30% by weight relative to the total weight of the composition.

The compositions used according to the invention generally comprise water or a mixture of water and of one or more organic solvents or a mixture of organic solvents.

The dye composition (A) and the oxidizing composition (B) according to the invention preferably comprise water.

Preferably, the water content ranges from 5% to 95% by weight, more preferentially from 10% to 90% by weight and better still from 20% to 80% by weight, relative to the total weight of composition (A).

The oxidizing composition (B) is generally an aqueous composition. For the purposes of the invention, the term "aqueous composition" means a composition comprising more than 20% by weight of water, preferably more than 30% by weight of water and even more advantageously more than 40% by weight of water.

The oxidizing composition (B) is generally an aqueous composition. The oxidizing composition (B) usually comprises water, which generally represents from 10% to 98% by weight, preferably from 20% to 96% by weight, preferably from 50% to 95% by weight, relative to the total weight of the composition.

pH of the Medium

The pH of composition (A) used in the process according to the invention generally ranges from 1 to 12. Preferably, the pH of composition (A) according to the invention is basic.

For the purposes of the present invention, the term "basic pH" means a pH above 7.

Preferably, the pH of composition (A) according to the invention is above 8, and particularly ranges from 8.5 to 12.

Preferably, the pH of the composition is between 9 and 12. Usually, the pH of composition (B) is less than 7. The pH of composition (B) of the invention is advantageously between 1 and 7, preferably between 1 and 4 and more preferentially from 1.5 to 3.5.

pH Adjuster

The cosmetically acceptable medium may be adjusted to the desired value by means of acidifying or basifying agents usually used in the dyeing of keratin fibers, or alternatively using standard buffer systems.

Among the acidifying agents, examples that may be mentioned include mineral acids, for instance hydrochloric acid, (ortho)phosphoric acid, boric acid, nitric acid or sulfuric acid, or organic acids, for instance compounds comprising at least one sulfonic acid function, a phosphonic acid function or a phosphoric acid function, or compounds bearing a carboxylic acid function such as those described previously.

Other Additives

The compositions used in the process according to the invention may also contain various additives conventionally used in hair dye compositions, such as mineral thickeners, and in particular fillers such as clays or talc; organic thickeners other than scleroglucan gums; antioxidants; penetrants; sequestrants; fragrances; dispersants; film-forming agents; ceramides; preserving agents; opacifiers; fatty substances and/or additional direct dyes.

The above additives are generally present in an amount for each of them of between 0.01% and 40% by weight relative to the weight of the composition, and preferably between 0.1% and 20% by weight relative to the weight of composition (A) and/or of composition (B).

Needless to say, a person skilled in the art will take care to select this or these optional additional compound(s) such that the advantageous properties intrinsically associated with the composition(s) that are useful in the dyeing process in accordance with the invention are not, or are not substantially, adversely affected by the envisioned addition(s).

Dispensing Device

The dispensing device according to the invention consists of a container comprising:
 i) at least two compartments (a) and (b) which are separate from each other,
  compartment (a) comprising a composition (A) comprising:
   one or more oxidation dyes;
   one or more alkaline agents; and
  compartment (b) comprising an oxidizing composition (B) comprising:
   one or more chemical oxidizing agents, preferably chosen from hydrogen peroxide and/or one or more systems for generating hydrogen peroxide, preferably from hydrogen peroxide; and
   one and/or the other of compositions (A) and/or (B) comprising one or more scleroglucan gums, preferably in a total weight content of greater than or equal to 0.5% relative to the total weight of composition(s) (A) and/or (B) containing same;
 ii) a dispensing means equipped with at least one dispensing orifice, in communication with compartments (a) and (b), for simultaneously dispensing compositions A and B, in mixed or separate form.

According to a particular embodiment, the dispensing device according to the invention consists of a container comprising:
 i) at least two compartments (a) and (b) which are separate from each other,
  compartment (a) comprising a composition (A) comprising:
   one or more oxidation dyes;
   one or more alkaline agents; and
  compartment (b) comprising an oxidizing composition (B) comprising:
   one or more chemical oxidizing agents, preferably chosen from hydrogen peroxide and/or one or more systems for generating hydrogen peroxide, preferably from hydrogen peroxide; and
   one and/or the other of compositions (A) and/or (B) comprising one or more scleroglucan gums in a total weight content of greater than or equal to 0.5% relative to the total weight of composition(s) (A) and/or (B) containing same;
 ii) a dispensing means equipped with at least one dispensing orifice, in communication with compartments (a) and (b), for simultaneously dispensing compositions A and B, in mixed or separate form.

According to a preferred embodiment of the invention, the dispensing device according to the invention consists of a container comprising:
 i) at least two compartments (a) and (b) which are separate from each other,
  compartment (a) comprising a composition (A) comprising:
   one or more oxidation dyes;
   one or more scleroglucan gums, preferably in a total amount of greater than or equal to 0.5% by weight relative to the total weight of composition (A);
   one or more alkaline agents; and
  compartment (b) comprising an oxidizing composition (B) comprising:
   one or more chemical oxidizing agents, preferably chosen from hydrogen peroxide and/or one or more systems for generating hydrogen peroxide, preferably from hydrogen peroxide; and
   one or more scleroglucan gums, preferably in a total weight content of greater than or equal to 0.5% relative to the total weight of composition (B);
 ii) a dispensing means equipped with at least one dispensing orifice, in communication with compartments (a) and (b), for simultaneously dispensing compositions A and B, in mixed or separate form.

According to an even more preferential embodiment, the dispensing device according to the invention consists of a container comprising:
 i) at least two compartments (a) and (b) which are separate from each other,
  compartment (a) comprising a composition (A) comprising:
   one or more oxidation dyes;
   one or more scleroglucan gums in a total amount of greater than or equal to 0.5% by weight relative to the total weight of composition (A);
   one or more alkaline agents; and
  compartment (b) comprising an oxidizing composition (B) comprising:
   one or more chemical oxidizing agents, preferably chosen from hydrogen peroxide and/or one or more systems for generating hydrogen peroxide, preferably from hydrogen peroxide; and one or more scleroglucan gums, preferably in a total weight content of greater than or equal to 0.5% relative to the total weight of composition (B);

ii) a dispensing means equipped with at least one dispensing orifice, in communication with compartments (a) and (b), for simultaneously dispensing compositions A and B, in mixed or separate form.

Preferably, the container of the device is pressurized (aerosol device). In other words, it comprises one or more propellant gases.

As propellant gases that are suitable for implementing the invention, mention may be made of the gases usually used in the cosmetics field, in particular optionally halogenated volatile hydrocarbons, for example n-butane, propane, isobutane, pentane, and halogenated derivatives thereof; carbon dioxide, nitrous oxide, dimethyl ether, nitrogen and oxygen, alone or as mixtures.

The walls of the container containing compartments (a) and (b) are preferably rigid, the container possibly being in this case a can, for example made of metal or plastic. According to a preferred embodiment, compartments (a) and (b) are flexible pouches. They may be made of metal, such as aluminum, or plastic.

According to this configuration, the propellant gas is in the volume defined between the walls of the container and the flexible pouches.

The device comprises a dispensing means equipped with at least one dispensing orifice, in communication with compartments (a) and (b), for simultaneously dispensing compositions (A) and (B), in separate form (for example side by side) or in mixture form, by means of at least one dispensing orifice.

Preferably, the means for dispensing the compositions comprises at least one dispensing valve. According to one embodiment, a valve is mounted on each compartment. According to one embodiment, a single valve is mounted on the compartments and connects them.

The valve(s) are in selective fluid communication with the inside of the compartment(s) via a valve inlet orifice, the communication being established in response to the actuation of an actuating means, such as a push-button.

The dispensing means of the device may comprise a diffuser which caps the valve(s). According to a preferred variant, the device comprises a single diffuser which caps the two valves. The push-button may form part of the diffuser.

The diffuser may be equipped with one or more dispensing pipes provided to convey the composition(s) to one or more dispensing orifices.

When the device comprises a single diffuser, it may be equipped with two composition conveying pipes, each pipe communicating with the outlet orifice of a valve.

According to a first embodiment, the two pipes each arrive at a dispensing orifice (not communicating with each other before the dispensing orifice). According to this configuration, the mixing of the compositions is performed only after they have been dispensed (thus after the dispensing orifices).

According to a second embodiment, the two pipes arrive at a mixing chamber equipped with a static mixer, from which a single pipe is directed to a single dispensing orifice. According to this configuration, the mixing of the compositions is performed just before they are expelled from the device.

Thus, compositions (A) and (B) can be dispensed in mixture form prior to application to the keratin fibers, or can be dispensed simultaneously in separate form, the mixing taking place after application to the keratin fibers (when the compositions leave simultaneously side by side).

Preferably, according to this embodiment, compartments (a) and (b) are flexible pouches, a dispensing valve being mounted on each of the compartments, a single diffuser capping the two valves.

It should be noted that the dispensing valve(s), and similarly the content of propellant gas(es), are adjusted so as to enable the dispensing of the compositions in appropriate respective proportions.

In practice, the dispensed composition (A)/composition (B) weight ratio ranges from 0.1 to 10, preferably from 0.2 to 2 and better still from 0.3 to 1.

Dyeing Process

A subject of the invention is also a process for dyeing keratin fibers, preferably human keratin fibers, using the device described previously.

According to a particular embodiment, a subject of the invention is also a process for dyeing keratin fibers, preferably human keratin fibers, using the device described previously.

More precisely, one subject of the invention is a process for dyeing keratin fibers, preferably human keratin fibers such as the hair, involving the application to the fibers:

a) of a dye composition (A) comprising:
  one or more oxidation dyes;
  ;
  one or more alkaline agents; and b) of an oxidizing composition (B) comprising:
  one or more chemical oxidizing agents, preferably chosen from hydrogen peroxide and/or one or more systems for generating hydrogen peroxide, preferably from hydrogen peroxide; and
  one and/or the other of compositions (A) and/or (B) comprising one or more scleroglucan gums in a total weight content of greater than or equal to 0.5% relative to the total weight of composition(s) (A) and/or (B) containing same;

compositions (A) and (B) being packaged in a device consisting of a container, preferably a pressurized container, comprising at least two compartments (a) and (b) which are separate from each other, compartment (a) comprising composition (A) and compartment (b) comprising composition (B), the device comprising a dispensing means equipped with at least one dispensing orifice, in communication with compartments (a) and (b), for dispensing compositions (A) and (B) simultaneously.

According to a preferred embodiment, a subject of the invention is a process for dyeing keratin fibers, preferably human keratin fibers such as the hair, involving the application to the fibers:

a) of a dye composition (A) comprising:
  one or more oxidation dyes;
  one or more scleroglucan gums, preferably in a total amount of greater than or equal to 0.5% by weight relative to the total weight of composition (A);
  one or more alkaline agents; and b) an oxidizing composition (B) comprising:
  one or more chemical oxidizing agents, preferably chosen from hydrogen peroxide and/or one or more systems for generating hydrogen peroxide, preferably from hydrogen peroxide; and
  one or more scleroglucan gums, preferably in a total weight content of greater than or equal to 0.5% relative to the total weight of (B);

compositions (A) and (B) being packaged in a device consisting of a container, preferably a pressurized container, comprising at least two compartments (a) and (b) which are separate from each other, compartment (a) comprising composition (A) and compartment (b) comprising composition (B), the device comprising a dispensing means equipped with at least one dispensing orifice, in communication with compartments (a) and (b), for dispensing compositions (A) and (B) simultaneously.

More preferentially, a subject of the invention is a process for dyeing keratin fibers, preferably human keratin fibers such as the hair, involving the application to the fibers:
a) of a dye composition (A) comprising:
  one or more oxidation dyes;
  one or more scleroglucan gums in a total amount of greater than or equal to 0.5% by weight relative to the total weight of composition (A);
  one or more alkaline agents; and
b) an oxidizing composition (B) comprising:
  one or more chemical oxidizing agents, preferably chosen from hydrogen peroxide and/or one or more systems for generating hydrogen peroxide, preferably from hydrogen peroxide; and
  one or more scleroglucan gums, preferably in a total weight content of greater than or equal to 0.5% relative to the total weight of (B);
compositions (A) and (B) being packaged in a device consisting of a container, preferably a pressurized container, comprising at least two compartments (a) and (b) which are separate from each other, compartment (a) comprising composition (A) and compartment (b) comprising composition (B), the device comprising a dispensing means equipped with at least one dispensing orifice, in communication with compartments (a) and (b), for dispensing compositions (A) and (B) simultaneously.

Compositions (A) and (B) dispensed by means of the device according to the invention are optionally mixed by massaging on the keratin fibers (in particular when compositions (A) and (B) are dispensed side by side), and left in place for a time generally from about 1 minute to 1 hour, preferably from 5 minutes to 30 minutes.

The temperature during the leave-on time is conventionally between room temperature (between 15° C. and 25° C.) and 80° C. and preferably between room temperature and 60° C.

After the treatment, the keratin materials are optionally rinsed with water, optionally subjected to washing followed by rinsing with water, and are then dried or left to dry.

Preferably, the keratin fibers are human keratin fibers, preferably human hair.

A subject of the invention is also a ready-to-use composition for dyeing keratin fibers, in particular human keratin fibers such as the hair, obtained by extemporaneous mixing, at the time of use, of a composition (A) as defined previously;
and of a composition (B) as defined previously.

According to a particular embodiment of the invention, the chemical oxidizing agent(s) preferably represent a total content ranging from 0.1% to 20% by weight, preferably from 0.5% to 15% by weight or even more preferentially from 1% to 10% by weight relative to the total weight of the ready-to-use composition (dispensed mixture of compositions A and B).

The examples that follow serve to illustrate the invention without, however, being limiting in nature.

In particular, the dyeing of the keratin fibers obtained in these examples may advantageously be evaluated in the CIE L*a*b* system, using a Datacolor Spectraflash SF600X spectrocolorimeter.

In this L*a*b* system, the three parameters respectively denote the intensity of the color (L*), the green/red color axis (a*) and the blue/yellow color axis (b*). The higher the value of L*, the lighter the color. The higher the value of a*, the redder the color and the higher the value of b*, the yellower the color.

The variation (or extent) of the dyeing between untreated locks of hair and locks of hair after treatment is defined by the parameter DE* and is calculated according to the following equation:

$$DE^* = \sqrt{(L^*-L_o^*)^2+(a^*-a_o^*)^2+(b^*-b_o^*)^2} \qquad (i)$$

In this equation, the parameters L*, a* and b* represent the values measured on locks of hair after dyeing and the parameters $L_0^*$, $a_0^*$ and $b_0^*$ represent the values measured on untreated locks of hair. The higher the DE* value, the better the dyeing of the keratin fibers.

In the CIE L*, a*, b* system, the chromaticity is calculated according to the following equation:

$$C^* = \sqrt{a^{*2}+b^{*2}}$$

The higher the value of C*, the more chromatic the coloring.

EXAMPLE 1

The following dye composition was prepared from the following ingredients in the following proportions indicated in grams:

|  | Composition A2 according to the invention Fiche formule |
|---|---|
| Ethanolamine | 3.23 |
| EDTA | 0.2 |
| Sodium sulfite | 0.5 |
| Toluene-2,5-diamine | 1.03 |
| 2,4-Diaminophenoxyethanol HCl | 0.021 |
| 2-Methylresorcinol | 0.27 |
| N,N-Bis(2-hydroxyethyl)-p-phenylenediamine sulfate | 0.13 |
| Resorcinol | 0.28 |
| m-Aminophenol | 0.45 |
| Fragrance | qs |
| Cetylhydroxyethylcellulose | 0.2 |
| Sclerotium gum | 1 |
| Water | qs 100 |
| Glycerol | 10 |
| Cocoyl betaine | 0.15 |
| Caprylyl/capryl glucoside | 0.6 |
| Ascorbic acid | 0.4 |

Visual Evaluation of the Stability of Composition A2

The stability of the dye compositions was evaluated by observing the compositions at T0 (immediately after preparation of the composition) and then after 2 months of storage at room temperature (25° C.), and after 2 months of storage at 45° C.

|  | Composition A2 according to the invention |
|---|---|
| Observation at T0 (immediately after preparation) | Homogeneous (no phase separation) Texture: Smooth gel |

| | Composition A2 according to the invention |
|---|---|
| Observation after 2 months at 25° C. | Homogeneous (no phase separation) Texture: Smooth gel |
| Observation after 2 months at 45° C. | Homogeneous (no phase separation) Texture: Smooth gel |

It is observed that composition A2 of the process according to the invention is homogeneous and forms a translucent gel at T0. After 2 months at room temperature or at 45° C.

The oxidizing composition B3 below was prepared from the following ingredients in the following proportions indicated in grams.

| | Fiche formule Oxidizing composition B3 according to the invention |
|---|---|
| Hydrogen peroxide | 6 |
| Phosphoric acid | qs pH 2.2 ± 0.2 |
| Tetrasodium etidronate | 0.2 |
| Tetrasodium pyrophosphate | 0.04 |
| Sodium salicylate | 0.035 |
| Sclerotium gum | 1.8 |
| Water | qs 100 |

It is observed that composition B3 of the process according to the invention is homogeneous and forms a translucent gel at T0, and after 2 months at room temperature or at 45° C.

Compositions A2 and B3 are packaged in an aerosol container comprising two flexible pouches equipped with a diffuser comprising a push-button and are dispensed simultaneously side by side in 1/1 proportions and are applied to locks of natural hair containing 90% white hairs.

The "mixture/lock" bath ratio is, respectively, 10/1 (g/g).

The compositions mix rapidly on the hair: the mixture is translucent and distributes easily and uniformly on the hair.

The working qualities are good: good wetting/glidant nature, good ease of application, good adhesion to the roots, good consistency on the head, good ease of extending the length of the fiber locks.

The leave-on time is 30 minutes, on a hotplate set at 27° C. On conclusion of the leave-on time, the locks are rinsed and then dried under a drying hood at 40° C.

The hair is then rinsed easily, and then washed with a standard shampoo and dried.

The color of the locks was evaluated in the CIE L*a*b* system, using a Datacolor Spectraflash SF600X spectrocolorimeter.

| | L* |
|---|---|
| Mixture of compositions A2 and B3 | 21.48 |

Intense coloring of the keratin fibers is obtained.

The invention claimed is:

1. A device for dispensing a product for dyeing keratin fibers, comprising a container comprising:
   (i) at least two compartments comprising a first compartment (a) and a second compartment (b) that are separate from each other, wherein:
      the first compartment (a) comprises a dye composition (A) comprising:
         at least one oxidation dye; and
         at least one alkaline agent chosen from aqueous ammonia, alkali metal or alkaline-earth metal metasilicates, alkanolamines, amino acids, or mixtures thereof;
      the second compartment (b) comprises an oxidizing composition (B) comprising at least one chemical oxidizing agent; and
      at least one of the dye composition (A) or the oxidizing composition (B) comprises at least one scleroglucan gum and is stable for at least two months at 25° C.; and
   (ii) a dispensing apparatus, equipped with at least one dispensing orifice in communication with compartments (a) and (b), configured to simultaneously dispense the dye composition (A) and the oxidizing composition (B), in mixed or separate form.

2. The device of claim 1, wherein the dye composition (A) comprises at least one scleroglucan gum, and the total amount of scleroglucan gums in the dye composition (A) is greater than or equal to 0.5% by weight, relative to the total weight of the dye composition (A), and/or the oxidizing composition (B) comprises at least one scleroglucan gum, and the total amount of scleroglucan gums in the oxidizing composition (B) is greater than or equal to 0.5% by weight, relative to the total weight of the oxidizing composition (B).

3. The device of claim 1, wherein the dye composition (A) comprises at least one scleroglucan gum, and the total amount of scleroglucan gums in the dye composition (A) ranges from 0.5% to 10% by weight, relative to the total weight of the dye composition (A).

4. The device of claim 1, wherein the at least one oxidation dye is chosen from benzene-based oxidation bases, or salts thereof; wherein the at least one oxidation dye is optionally combined with at least one coupler chosen from meta-phenylenediamines, meta-aminophenols, meta-diphenols, naphthalene-based couplers, heterocyclic couplers, salts thereof, or mixtures thereof.

5. The device of claim 1, wherein the at least one oxidation dye is chosen from para-phenylenediamines, bis (phenyl)alkylenediamines, para-aminophenols, ortho-aminophenols, heterocyclic bases, salts thereof, or mixtures thereof.

6. The device of claim 1, wherein the alkaline agent comprises at least one mineral alkaline agent chosen from aqueous ammonia, alkali metal metasilicates, and/or alkaline-earth metal metasilicates, and at least one organic alkaline agent chosen from alkanolamines and/or amino acids.

7. The device of claim 1, wherein the at least one alkaline agent comprises monoethanolamine.

8. The device of claim 1, wherein the dye composition (A) further comprises at least one surfactant chosen from cationic surfactants, nonionic surfactants, or mixtures thereof; wherein the total amount of surfactants chosen from cationic surfactants, nonionic surfactants, or mixtures thereof in the dye composition (A) ranges from 0.01% to 20% by weight, relative to the total weight of the dye composition (A).

9. The device of claim 1, wherein the dye composition (A) further comprises at least one associative polymer; wherein the total amount of associative polymers in the dye composition (A) ranges from 0.01% to 10% by weight, relative to the total weight of the dye composition (A).

10. The device of claim 9, wherein the at least one associative polymer is nonionic, chosen from celluloses modified with groups including at least one fatty chain.

11. The device of claim 9, wherein the dye composition (A) further comprises at least one cationic polymer chosen from:
(1) cyclopolymers of alkyldiallylamine or of dialkyldiallylammonium, comprising homopolymers or copolymers including, as main constituent of the chain, units corresponding to formula (I) or (II):

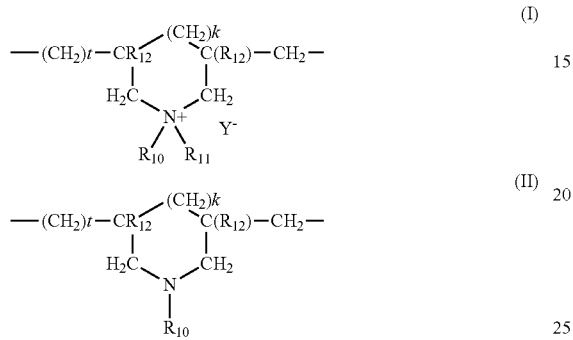

wherein in formulae (I) and (II):
k and t are equal to 0 or 1, the sum k+t being equal to 1;
$R_{12}$ denotes a hydrogen atom or a methyl radical;
$R_{10}$ and $R_{11}$, independently of each other, are chosen from a $C_1$-$C_6$ alkyl group, a $C_1$-$C_5$ hydroxyalkyl group, or a $C_1$-$C_4$ amidoalkyl group; or alternatively, $R_{10}$ and $R_{11}$ denote, together with the nitrogen atom to which they are attached, a heterocyclic group;
$Y^-$ is an anion chosen from bromide, chloride, acetate, borate, citrate, tartrate, bisulfate, bisulfite, sulfate, or phosphate; or
(2) quaternary diammonium polymers comprising repeating units of formula (III):

wherein in formula (III):
$R_{13}$, $R_{14}$, $R_{15}$, and $R_{16}$, which may be identical or different, are chosen from aliphatic radicals, alicyclic radicals, or arylaliphatic radicals comprising from 1 to 20 carbon atoms, $C_1$-$C_{12}$ hydroxyalkyl aliphatic radicals, or mixtures thereof; alternatively, $R_{13}$, $R_{14}$, $R_{15}$, and $R_{16}$, together or separately, form, with the nitrogen atoms to which they are attached, heterocycles optionally comprising a second non-nitrogen heteroatom; or alternatively, $R_{13}$, $R_{14}$, $R_{15}$, and $R_{16}$ represent a linear or branched $C_1$-$C_6$ alkyl radical substituted with a nitrile, an ester, an acyl, an amide, a —CO—O—$R_{17}$-D, or a —CO—NH—$R_{17}$-D group, wherein $R_{17}$ is an alkylene and D is a quaternary ammonium group;
$A_1$ and $B_1$ are chosen from linear or branched, saturated or unsaturated, divalent polymethylene groups comprising from 2 to 20 carbon atoms, which may contain, linked to, or intercalated in the main chain, at least one aromatic ring, at least one group chosen from oxygen atom, sulfur atom, sulfoxide, sulfone, disulfide, amino, alkylamino, hydroxyl, quaternary ammonium, ureido, amide, ester groups, or mixtures thereof; and
$X^-$ denotes an anion derived from a mineral or organic acid;
wherein $A_1$, $R_{13}$, and $R_{15}$ can form, with the two nitrogen atoms to which they are attached, a piperazine ring;
wherein if $A_1$ denotes a linear or branched, saturated or unsaturated alkylene or hydroxyalkylene radical, $B_1$ denotes a group $(CH_2)_n$—CO-D-OC—$(CH_2)_p$—, wherein n and p, which may be identical or different, are integers ranging from 2 to 20, and D is chosen from:
a) a glycol residue of formula —O—Z—O—, wherein Z is chosen from a linear or branched hydrocarbon-based radical or a group corresponding to one of the following formulae: —($CH_2CH_2O$)x-$CH_2CH_2$—, and —[$CH_2CH(CH_3)O$]y-$CH_2CH(CH_3)$—, wherein x and y denote an integer from 1 to 4, representing a defined and unique degree of polymerization, or x and y denote any number from 1 to 4, representing an average degree of polymerization;
b) a bis-secondary diamine residue;
c) a bis-primary diamine residue of formula —NH—Y—NH—, wherein Y denotes a linear or branched hydrocarbon-based radical, or alternatively, the divalent radical —$CH_2$—$CH_2$—S—S—$CH_2$—$CH_2$_13 ; and
d) a ureylene group of formula —NH—CO—NH—.

12. The device of claim 11, wherein the at least one cationic polymer has a number-average molar mass (Mn) ranging from 1000 to 100000.

13. The device of claim 11, wherein the at least one cationic polymer is chosen from:
(1) dialkyldiallylammonium homopolymers; and/or
(2) cationic polymers that are constituted of repeating units corresponding to the formula (IV):

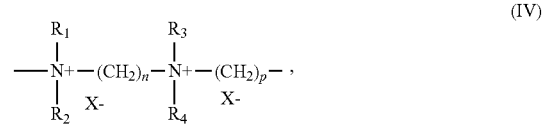

wherein in formula (IV), $R_1$, $R_2$, $R_3$, and $R_4$, which may be identical or different, are chosen from an alkyl or hydroxyalkyl radical containing from 1 to 4 carbon atoms, n and p are integers ranging from 2 to 20, and $X^-$ is an anion derived from a mineral or organic acid.

14. The device of claim 1, wherein the oxidizing composition (B) comprises at least one scleroglucan gum, and the total amount of scleroglucan gums in the oxidizing composition (B) ranges from 0.5% to 10% by weight, relative to the total weight of the oxidizing composition (B).

15. The device of claim 1, wherein the at least one chemical oxidizing agent is chosen from hydrogen peroxide and/or at least one system generating hydrogen peroxide.

16. The device of claim 1, wherein the container is pressurized and comprises at least one propellant gas.

17. The device of claim 16, wherein the first compartment (a) and the second compartment (b) are flexible pouches, and the at least one propellant gas is in a volume defined between a wall of the container and the flexible pouches.

18. A method for dyeing keratin fibers, comprising applying to the keratin fibers:
- a) a dye composition (A) comprising:
  - at least one oxidation dye, and
  - at least one alkaline agent chosen from aqueous ammonia, alkali metal or alkaline-earth metal metasilicates, alkanolamines, amino acids, or mixtures thereof; and
- b) an oxidizing composition (B) comprising at least one chemical oxidizing agent;

wherein at least one of the dye composition (A) or the oxidizing composition (B) comprises at least one scleroglucan gum and is stable for at least two months at 25° C.;

wherein the dye composition (A) and the oxidizing composition (B) are packaged in a device comprising a container comprising at least two compartments comprising a first compartment (a) and a second compartment (b) that are separated from each other;

wherein the first compartment (a) comprises the dye composition (A) and the second compartment (b) comprises the oxidizing composition (B); and wherein the device comprises a dispensing means equipped with at least one dispensing orifice, in communication with the first compartment (a) and the second compartment (b), for dispensing the dye composition (A) and the oxidizing composition (B) simultaneously.

19. The method of claim 18, wherein the total amount of scleroglucan gums in the dye composition (A) ranges from 0.5% to 10% by weight, relative to the total weight of the dye composition (A), and/or the total amount of scleroglucan gums in the oxidizing composition (B) ranges from 0.5% to 10% by weight, relative to the total weight of the oxidizing composition (B).

20. The method of claim 18, wherein the total amount of scleroglucan gums in the dye composition (A) ranges from 0.5% to 3% by weight, relative to the total weight of the dye composition (A), and/or the total amount of scleroglucan gums in the oxidizing composition (B) ranges from 0.5% to 3% by weight, relative to the total weight of the oxidizing composition (B).

* * * * *

UNITED STATES PATENT AND TRADEMARK OFFICE
CERTIFICATE OF CORRECTION

PATENT NO. : 11,701,311 B2
APPLICATION NO. : 17/253019
DATED : July 18, 2023
INVENTOR(S) : Sabrina Muller et al.

It is certified that error appears in the above-identified patent and that said Letters Patent is hereby corrected as shown below:

In the Claims

Claim 11, Column 26, Line 34, replace "CH2_13" with "CH2-".

Signed and Sealed this
Thirtieth Day of January, 2024

Katherine Kelly Vidal
*Director of the United States Patent and Trademark Office*